(12) United States Patent
Clark et al.

(10) Patent No.: US 8,939,364 B2
(45) Date of Patent: Jan. 27, 2015

(54) CONTAMINATION CONTROL FOR LIQUID HANDLING

(75) Inventors: Craig B. Clark, San Diego, CA (US);
John M. Gilker, San Diego, CA (US);
Norbert D. Hagen, Carlsbad, CA (US);
Tom R. Horn, San Diego, CA (US);
Byron J. Knight, San Diego, CA (US);
David Opalsky, San Diego, CA (US);
Jason F. Rhubottom, Oceanside, CA (US); Waldemar Lukhaub, Vaihingen/Enz. (DE); Olaf Hörger, Neuenbürg (DE)

(73) Assignees: Gen-Probe Incorporated, San Diego, CA (US); Stratec Biomedical AG, Birkenfeld-Graefenhausen (DE)

( * ) Notice: Subject to any disclaimer, the term of this patent is extended or adjusted under 35 U.S.C. 154(b) by 296 days.

(21) Appl. No.: 13/320,749

(22) PCT Filed: May 17, 2010

(86) PCT No.: PCT/US2010/035146
§ 371 (c)(1),
(2), (4) Date: Feb. 2, 2012

(87) PCT Pub. No.: WO2010/132887
PCT Pub. Date: Nov. 18, 2010

(65) Prior Publication Data
US 2012/0261469 A1 Oct. 18, 2012

Related U.S. Application Data

(60) Provisional application No. 61/178,652, filed on May 15, 2009.

(51) Int. Cl.
*G06K 19/00* (2006.01)
*G06Q 10/08* (2012.01)
(Continued)

(52) U.S. Cl.
CPC ............... *G06Q 10/087* (2013.01); *B01L 9/06* (2013.01); *G01N 35/1004* (2013.01);
(Continued)

(58) Field of Classification Search
USPC ......... 235/375, 385, 435, 439, 451, 462, 487, 235/492; 340/10, 572
See application file for complete search history.

(56) References Cited

U.S. PATENT DOCUMENTS 5,036,001 A 7/1991 Gork et al.
(Continued)

FOREIGN PATENT DOCUMENTS

EP 0979999 A2 2/2000
(Continued)

OTHER PUBLICATIONS

International Search Report and Written opinion in PCT/US2010/035146, Dec. 27, 2010.
(Continued)

*Primary Examiner* — Matthew Mikels
(74) *Attorney, Agent, or Firm* — Rothwell, Figg, Ernst & Manbeck PC; Charles B. Cappellari, Esq.

(57) ABSTRACT

A structure (10) for holding sample-containing receptacles includes a cover (40) with holes formed therein through which the receptacles can be accessed with a substance transfer mechanism, such as a robotic pipettor. When the transfer mechanism is inserted into and then withdrawn from a receptacle, a string of viscous material may be suspended from the mechanism. A viscous string removal element (44) adjacent each opening (42) engages the string of viscous material and dislodges the string from the mechanism when the mechanism moves in a prescribed path with respect to the removal element. A sample rack configured to hold receptacles and to be inserted into the structure below the cover includes a sample rack having receptacle-receiving pockets, each with a resilient element and a positioning feature for holding receptacles of varying sizes in a predetermined position within the receptacle receiving pocket, and a cover including features for preventing a receptacle from being pulled out of its receptacle-receiving pocket when the transfer mechanism is withdrawn from the receptacle.

18 Claims, 14 Drawing Sheets

(51) Int. Cl.
  *B01L 9/06* (2006.01)
  *G01N 35/10* (2006.01)

(52) U.S. Cl.
  CPC ........ *B01L 2200/023* (2013.01); *B01L 2200/06* (2013.01); *B01L 2200/141* (2013.01); *B01L 2300/021* (2013.01)
  USPC ........... 235/385; 235/375; 235/435; 235/439; 235/454

(56) References Cited

U.S. PATENT DOCUMENTS

| | | | |
|---|---|---|---|
| 5,700,429 | A | 12/1997 | Bühler et al. |
| 5,861,563 | A | 1/1999 | Boyd et al. |
| 6,060,022 | A | 5/2000 | Pang et al. |
| 6,426,044 | B1 | 7/2002 | Cohen et al. |
| 6,579,711 | B1 | 6/2003 | Gaier et al. |
| 6,587,031 | B1 * | 7/2003 | Daugherty et al. .......... 340/5.31 |
| 7,282,182 | B2 | 10/2007 | Dale et al. |
| 7,547,556 | B2 | 6/2009 | Hunter et al. |
| 7,640,769 | B1 * | 1/2010 | Clark .............................. 62/440 |
| 7,910,067 | B2 | 3/2011 | Knight et al. |
| 2003/0038071 | A1 | 2/2003 | Hansen et al. |
| 2004/0005714 | A1 | 1/2004 | Safar et al. |
| 2004/0195193 | A1 | 10/2004 | Jafari et al. |
| 2005/0079105 | A1 | 4/2005 | Hunter et al. |
| 2005/0230470 | A1 * | 10/2005 | Hoshino ....................... 235/375 |
| 2006/0266719 | A1 | 11/2006 | Knight et al. |
| 2008/0261210 | A1 | 10/2008 | Frantzen et al. |
| 2008/0314980 | A1 * | 12/2008 | Folcke et al. ................. 235/385 |
| 2009/0220379 | A1 | 9/2009 | Wakamiya et al. |
| 2010/0075426 | A1 | 3/2010 | Kubo et al. |

FOREIGN PATENT DOCUMENTS

| | | |
|---|---|---|
| EP | 1447669 A2 | 8/2004 |
| EP | 1447669 A3 | 8/2004 |
| EP | 2073017 A1 | 6/2009 |
| EP | 2080553 A1 | 7/2009 |
| WO | 9401781 A1 | 1/1994 |
| WO | 03008099 A2 | 1/2003 |
| WO | 03008099 A3 | 1/2003 |
| WO | 03097240 A2 | 11/2003 |
| WO | 2005093433 A1 | 10/2005 |
| WO | 2007121324 A1 | 10/2007 |
| WO | 2008044594 A1 | 4/2008 |

OTHER PUBLICATIONS

Invitation to Pay Additional Fees, including Partial International Search Report in PCT/US2010/035146, Sep. 17, 2010.
PCT International Preliminary Report on Patentability, International Application No. PCT/US2010/035146, Nov. 24, 2011.

* cited by examiner

CONTAMINATION CONTROL FOR LIQUID HANDLING

CROSS-REFERENCE TO RELATED APPLICATIONS

This application is the National Stage pursuant to 35 U.S.C. §371 of PCT International Application No. PCT/US10/35146, which claims the benefit of U.S. Provisional Application Number 61/178,652, filed on May 15, 2009, the disclosure of each of which is incorporated by reference herein in its entirety.

BACKGROUND

1. Field of the Invention

This invention relates to systems, methods, and apparatus for storing and presenting sample materials for access by a sample transfer apparatus and for limiting the incidence of cross-contamination between sample-containing vessels during a sample transfer operation.

2. Background of the Invention

All documents referred to herein, or the indicated portions, are hereby incorporated by reference herein. No document, however, is admitted to be prior art to the claimed subject matter.

Analyzers for performing assays on fluid samples typically include a fluid transfer mechanism for transferring fluid sample material and other fluids between various receptacles or containers. For example, fluid sample material may be introduced into the analyzer via a sample receptacle, such as a test tube, containing an amount of the fluid sample, placed in the analyzer or in operative proximity to the analyzer. The analyzer may include an automated fluid transfer mechanism comprising a robotically-controlled pipetting device having an aspirating probe for accessing the contents of a receptacle. The probe may comprises a barrel with a protective tip (e.g., a pipette tip) mounted (e.g., frictionally) on its distal end.

Fluid sample material is transferred from the sample receptacle by positioning the aspirating probe above the sample receptacle and then lowering the probe until a distal end of the probe is submerged in the fluid sample material held in the container. After the probe is submerged, an amount of fluid is drawn into the probe. The probe is then raised and moved to another location within the analyzer and is operatively positioned above another container (or, alternatively, the probe can be held in a fixed position and the sample receptacle and other containers can be moved relative to the probe). The sample material may be transferred to a reaction receptacle (e.g., test tube, cuvette, microtiter plate well, etc.) within which the sample material is combined with reagents and/or other reactants (and, optionally, the container and its contents may be subjected to other conditions or stimuli, such as, incubation at an elevated temperature, mixing, and/or centrifuging) to effect a transformation or chemical, biochemical or biological reaction. After the probe is positioned above the container that is to receive the sample material, some or all of the fluid is dispensed from the probe into one or more containers, moving the probe from receiving container to receiving container as necessary.

During such a fluid transfer procedure, care must be taken to avoid cross-contamination due to spilled or misplaced sample material. For example, sample from one sample receptacle should not be mistakenly deposited into another sample receptacle containing a different sample or a sample from a different source. Similarly, no sample material should be deposited into a reaction receptacle in which such sample is not intended, for example in a reaction receptacle within which a different sample had already been dispensed.

Fluid sample material may include, for example, urine, blood, plasma, saliva, mucus, seminal fluid, amniotic fluid, cerebrospinal fluid, synovial fluid, and cultures. Such materials may, under certain circumstances or conditions, be characterized as having a viscous consistency. Accordingly, when the probe of a pipetting device is submerged into the sample material and is then withdrawn, the viscous or mucoid nature of the sample material may result in a string of viscous material suspended from a distal end of the probe after the probe is withdrawn from the sample receptacle. Further movement of the sample transfer probe may drag the string of viscous material along with it, thereby potentially causing cross-contamination should the string of viscous material contact or fall into another sample receptacle or reaction vessel or other contamination-sensitive surface or component within the analyzer.

SUMMARY OF THE INVENTION

The present invention provides methods, systems, and apparatus for removing a string of viscous material from the probe of a fluid transfer mechanism in a controlled manner so that the string is detached from the probe in a location that is unlikely to cause cross-contamination.

Aspects of the invention are embodied in a method for separating a viscous material suspended from a probe of an automated pipettor. The probe is lowered into a receptacle containing a viscous material through an opening formed in a cover disposed over the receptacle. At least a portion of the viscous material is drawn into the probe. The probe from is then removed from the vessel to a position above the cover, whereby a string of the viscous material is suspended from the probe. The probe is then moved laterally with respect to the opening to a position offset from the opening and adjacent a raised structure formed on the cover. Next, the probe is moved laterally along a path comprising movement in first and second directions. The transition from movement in the first direction to movement in the second direction causes the string of viscous material to contact the raised structure, and the continued movement of the probe along the path causes at least a portion of the string of viscous material to be separated from the probe.

In one embodiment, the raised structure includes first and second upright, non-coplanar sides defining a corner at a transition therebetween, and the transition from movement in the first direction to movement in the second causes the string of viscous material to contact the corner of the raised structure.

In one embodiment, the first and second directions are substantially at right angles to one another, and, in another embodiment, the first and second directions are not at right angles to one another.

In one embodiment, after moving the probe laterally with respect to the opening to a position offset from the opening and adjacent the raised structure, the probe is lowered so that the distal end thereof is disposed below the top of the raised structure.

In one embodiment, the probe comprises a barrel with a protective tip mounted on a distal end thereof Further aspects of the invention are embodied in a system for transferring viscous materials. The system comprises a sample holding area, an automated pipettor, and a controller. The sample holding area is configured to receive and position a plurality of receptacles and includes a cover member having a plurality of openings through which the automated pipettor can access the receptacles positioned beneath the cover member. The openings are arranged so that each opening is associated with one of the receptacles, and a top side of the cover member includes a plurality of raised structures. Each raised structure is adjacent to one of the openings. The automated pipettor is operatively associated with the sample holding area and is configured for automated movement with respect to the sample holding area and includes a fluid transfer probe. The controller controls movement of the probe of the pipettor, and is programmed to selectively move the probe into a position aligned with one of the openings, lower the probe through the opening and into the associated receptacle below the opening, raise the probe out of the associated receptacle to a position above the cover member, move the probe laterally to a position offset from the opening and adjacent the raised structure associated with the opening with the distal end of the probe disposed below a top surface of the associated raised structure, and move the probe laterally, relative to the associated raised structure, along a path comprising movement in first and second directions, the transition from the first direction to the second direction causing the string of viscous material suspended from the probe to contact the raised structure.

In one embodiment, the probe comprises a pipette with a protective tip mounted on a distal end thereof In one embodiment, the controller is programmed to move the probe in first and second directions that are substantially at right angles to one another, and, in another embodiment, the controller is programmed to move the probe in first and second directions that are not at right angles to one another.

In one embodiment, the controller is programmed to lower the probe after moving the probe to the position offset from the opening so that the distal end thereof is disposed below the top of the raised structure.

In one embodiment, the plurality of openings are arranged in an array pattern of aligned rows and columns of openings.

In one embodiment, each raised structure comprises two opposed and generally parallel sides and an end wall spanning the ends of the two sides. In another embodiment, each raised structure further comprises a raised ledge spanning ends of the two sides opposite the end wall, and the sides and the end wall are higher than the raised ledge.

In one embodiment, each raised structure is a U-shaped structure at least partially surrounding the opening, and movement of the probe laterally with respect to the opening to a position offset from the opening comprises moving the probe through an opening defined between opposed legs of the U-shaped structure.

In other embodiments, each raised structure may comprises a square element surrounding the opening, a triangular element surrounding the opening, or a hexagonal element surrounding the opening.

In one embodiment, each raised structure comprises a raised surface surrounding the opening and a post projecting above the raised surface adjacent the opening.

In one embodiment, the system further includes a cooling system constructed and arranged to maintain the sample holding area a cooler than ambient temperature.

In one embodiment, the system further includes a label reading device constructed and arranged to a read machine readable label placed on each of said receptacles.

In one embodiment, the label reading device comprises a barcode reader.

In one embodiment, the system further includes one or more receptacle holders, each configured to hold a plurality of receptacles, and the sample receiving area is configured to receive said receptacle holders and includes guide structures to ensure the proper position and orientation of the receptacles carried in each rack relative to the openings formed in said cover member.

In one embodiment, the guide structures define two or more lanes configured to receive a different one of the receptacle holders.

In one embodiment, the raised structure comprises two generally upright, non-coplanar sides defining a corner at a transition therebetween, and the controller is programmed to selectively move the probe laterally, relative to the corner of the associated raised structure, along the path comprising movement in first and second directions, and wherein the transition from the first direction to the second direction causes the string of viscous material suspended from the probe to contact the corner of the associated raised structure In one embodiment, the system further includes indicator elements in communication with said controller and configured to indicate which of two or more lanes is to receive the next receptacle holder to be inserted into the sample receiving area.

In one embodiment, the system further includes a rack sensing element configured to detect if a rack is fully inserted into the sample receiving area.

In one embodiment, the plurality of openings are arranged in parallel rows with openings in adjacent rows being offset from one another.

In one embodiment, the sample holding area comprises a sample bay having first and second side walls and a back wall extending between said first and second side wall, and first and second side walls and said back wall support said cover member.

In one embodiment, the first and second side walls and said back wall are insulated.

In one embodiment, the system further includes a floor plate with a coolant tube arranged below said floor plate and configured to carry a cooling medium for cooling said sample bay.

Further aspects of the invention are embodied in a sample rack for carrying a plurality of receptacles, which may be of different sizes. The sample rack includes a receptacle holder and a cover configured to be releasably secured to the receptacle holder. The receptacle holder includes a plurality of receptacle-receiving pockets, a receptacle positioning feature associated with each of said receptacle-receiving pockets, and a resilient element associated with each of said receptacle-receiving pockets. Each receptacle-receiving pocket is configured to receive a receptacle, and each resilient element is configured to urge the receptacle into said positioning feature to hold the receptacle in a fixed, predetermined position within said receptacle-receiving pocket. The cover includes a transverse wall including a plurality of spaced-apart receptacle access openings formed in said transverse wall, each receptacle access opening being associated with one receptacle-receiving pocket. And the cover also includes a receptacle-retaining element associated with each receptacle-receiving pocket and configured to engage a portion of the top of a receptacle urged into the predetermined position within each receptacle-receiving pocket to prevent the receptacle from being lifted out of the receptacle-receiving pocket.

In one embodiment, the receptacle holder comprises a base and a plurality of divider walls extending upwardly at spaced-apart positions from said base and defining said receptacle-receiving pockets in the spaces between adjacent pairs of divider walls. Each receptacle positioning feature is disposed along one side of each of said receptacle-receiving pockets, and each resilient element is disposed along one side of each of said receptacle-receiving pockets opposite said positioning feature.

In one embodiment, each positioning feature comprises a V-shaped notch formed on one side of each divider wall In one embodiment, each resilient element comprises a spring clip including one portion attached to a divider wall defining one side of the receptacle-receiving pocket and another portion projecting from the divider wall into the receptacle-receiving pocket.

In one embodiment, the sample rack further includes a handle associated with said receptacle holder.

In one embodiment, a guide slot formed is formed in a bottom side of the base, and said guide slot is configured to engage a guide rail within an apparatus configured to receive the sample rack.

In one embodiment, the sample rack further includes a machine readable label.

In one embodiment, the receptacle-receiving pockets are arranged in an aligned configuration.

In one embodiment, the receptacle-receiving pocket is configured to receive a cylindrical test tube of any of a plurality of different diameters.

In one embodiment, the cover is made from a transparent or translucent material.

In one embodiment, the cover includes opposed side walls, upper divider walls, and lower divider walls. The transverse wall extends between the opposed side walls with a portion of each side wall extending above said transverse wall and a portion of each side wall extending below said transverse wall. The upper divider walls project above said transverse wall and extend across said transverse wall from one side wall to the other side wall with one upper divider wall disposed between each adjacent pair of access openings. The lower divider walls project below the transverse wall and extend across said transverse wall from one side wall to the other side wall with one lower divider wall disposed between each adjacent pair of access openings.

In one embodiment, the receptacle retaining element associated with each receptacle-receiving pocket comprises a notch formed in each lower divider wall.

Further aspects of the invention are embodied in a method for reading machine-readable labels disposed on receptacles carried on a receptacle rack that is placed in an apparatus comprising a plurality of rack-receiving locations. Each rack-receiving location is configured to receive a rack holding at least one receptacle. The apparatus further includes a label-reading device configured to read a rack-identifying machine-readable label disposed on the rack and machine-readable labels disposed on the at least one receptacle held on the rack, and the label reading device is disposed adjacent to one of the rack-receiving locations. A rack holding at least one receptacle having a machine readable label disposed thereon is placed in the rack-receiving location disposed adjacent to the label reading device. During or after placing the rack, the machine-readable label of each receptacle having a machine-readable label is read to obtain receptacle data and the rack-identifying machine readable label is read to obtain rack identifying data. The receptacle data obtained and the rack identifying data obtained are stored, and the receptacle data is associated with the rack identifying data. The rack is then removed from the rack-receiving location disposed adjacent to the label-reading device. Next, the is placed in one of the other rack-receiving locations. During or after placing the rack in one of the other rack-receiving locations, the rack-identifying machine readable label is read to obtain rack identifying data. Location data identifying the rack-receiving location in which the rack was placed is acquired. The stored receptacle data that is associated with the rack-identifying data is retrieved, and the retrieved receptacle data is associated with the acquired location data to thereby associate the retrieved receptacle data with the rack-receiving location in which the rack was placed.

In one embodiment, the method further includes the step of reading receptacle position-identifying machine readable labels to obtain receptacle position data for each receptacle having a machine-readable label.

In one embodiment, the machine-readable labels are barcode labels and the label reading device is a barcode reader.

In one embodiment, the rack-receiving location comprises a linear track adapted to receive a rack configured to hold a plurality of receptacles in an aligned orientation.

In one embodiment, the method further includes the step of providing an indication of the rack-receiving location in which the rack should be placed after removing the rack from the rack-receiving location adjacent to the label reading device, and, in another embodiment, the method further includes the step of determining whether the rack was placed in the indicated location.

In one embodiment, the method further includes the step of measuring the time lapsed between removing the rack from the rack-receiving location adjacent to the label reading device and placing the rack in one of the other rack-receiving locations, and, in another embodiment, whether the time lapsed is within a specified period of time is determined.

Further aspects of the invention are embodied in an apparatus for reading machine-readable labels disposed on receptacles and associating receptacle data read from each machine-readable label with a location within the system. The apparatus includes a plurality of rack-receiving locations, a label reading device, and a data processing system. Each of the rack-receiving locations is configured to receive a rack holding at least one receptacle. The label reading device is configured to read a rack-identifying machine-readable label disposed on the rack and machine-readable labels disposed on receptacles held on the rack, and the label reading device is disposed adjacent to one of said rack-receiving locations. The data processing system includes data storage media and is configured to read the machine-readable label of each receptacle having a machine-readable label and read the rack-identifying machine readable label when the rack is placed into said rack-receiving location disposed adjacent to said label reading device to obtain receptacle data for each receptacle having a machine-readable label and to obtain rack identifying data. The data processing system stores the receptacle data and the rack identifying data and associates the receptacle data with the rack identifying data. The data processing system reads the rack-identifying machine readable label when the rack is placed in one of the other rack-receiving locations to obtain rack identifying data. The data processing system acquires location data identifying the other rack-receiving location in which the rack was placed. And the data processing system retrieves the stored receptacle data that is associated with the rack-identifying data and associates the retrieved receptacle data with the location data to thereby associate the retrieved receptacle data with the rack-receiving location in which the rack was placed.

In one embodiment, the machine readable labels are barcode labels and the label reading device is a barcode reader.

In one embodiment, each rack-receiving location comprises a linear track adapted to receive a rack configured to hold a plurality of receptacles in an aligned orientation.

In one embodiment, the data processing system is further configured to provide an indication of the rack-receiving location in which a rack should be placed.

In one embodiment, the apparatus further comprises a rack configured to hold one or more receptacles and includes a rack-identifying machine-readable label.

These and other features, aspects, and advantages of the present invention will become apparent to those skilled in the art after considering the following detailed description, appended claims and accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF THE INVENTION

Figure 1:
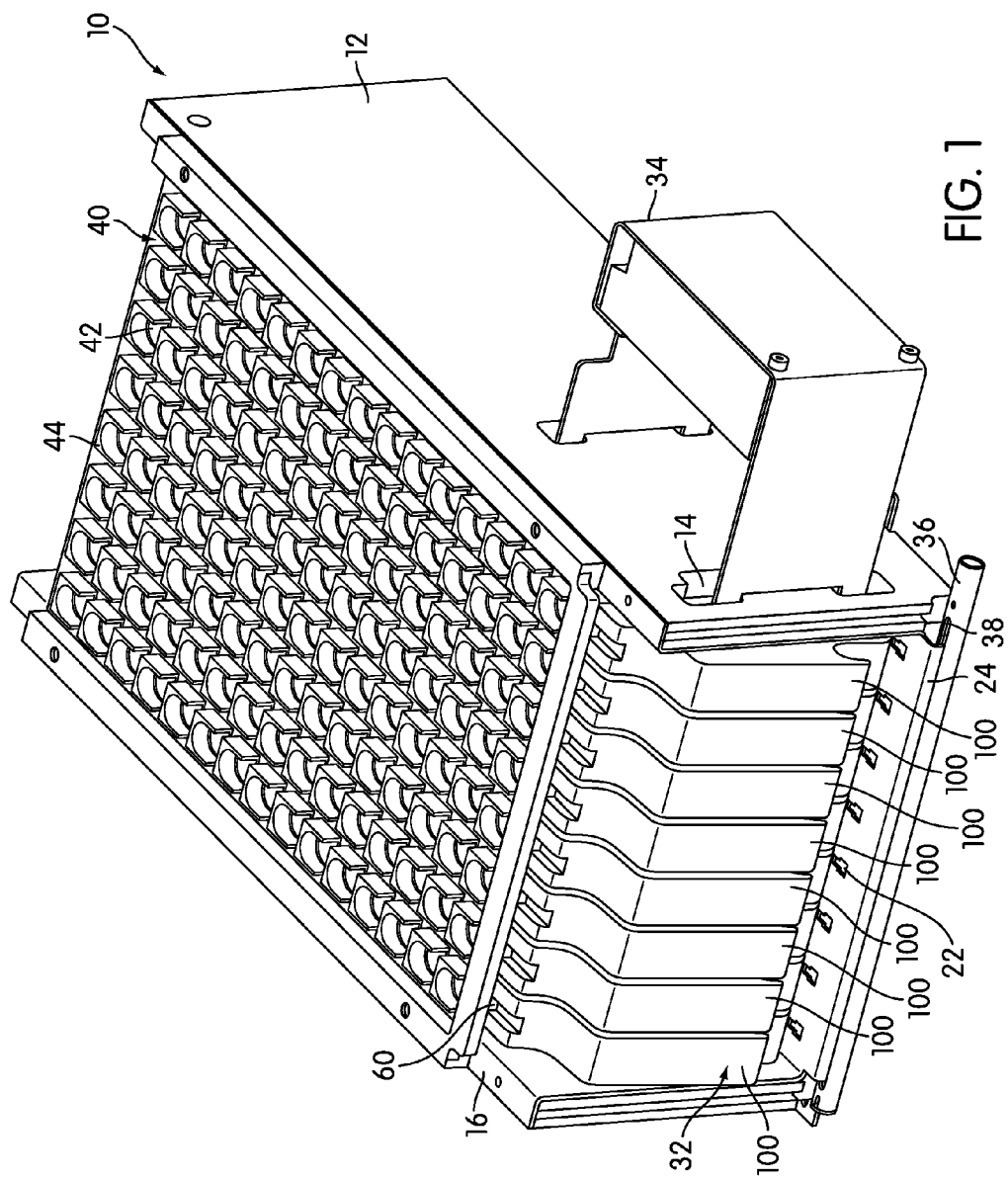
FIG. 1 is an upper front perspective view of a sample receptacle module embodying aspects of the present invention.

As shown in FIG. 1, a sample receptacle module embodying aspects of the present invention includes a sample bay 10 within which are disposed a plurality of sample racks 100. In the illustrated embodiment, the sample bay 10 holds up to eight sample racks 100.

Figure 2:
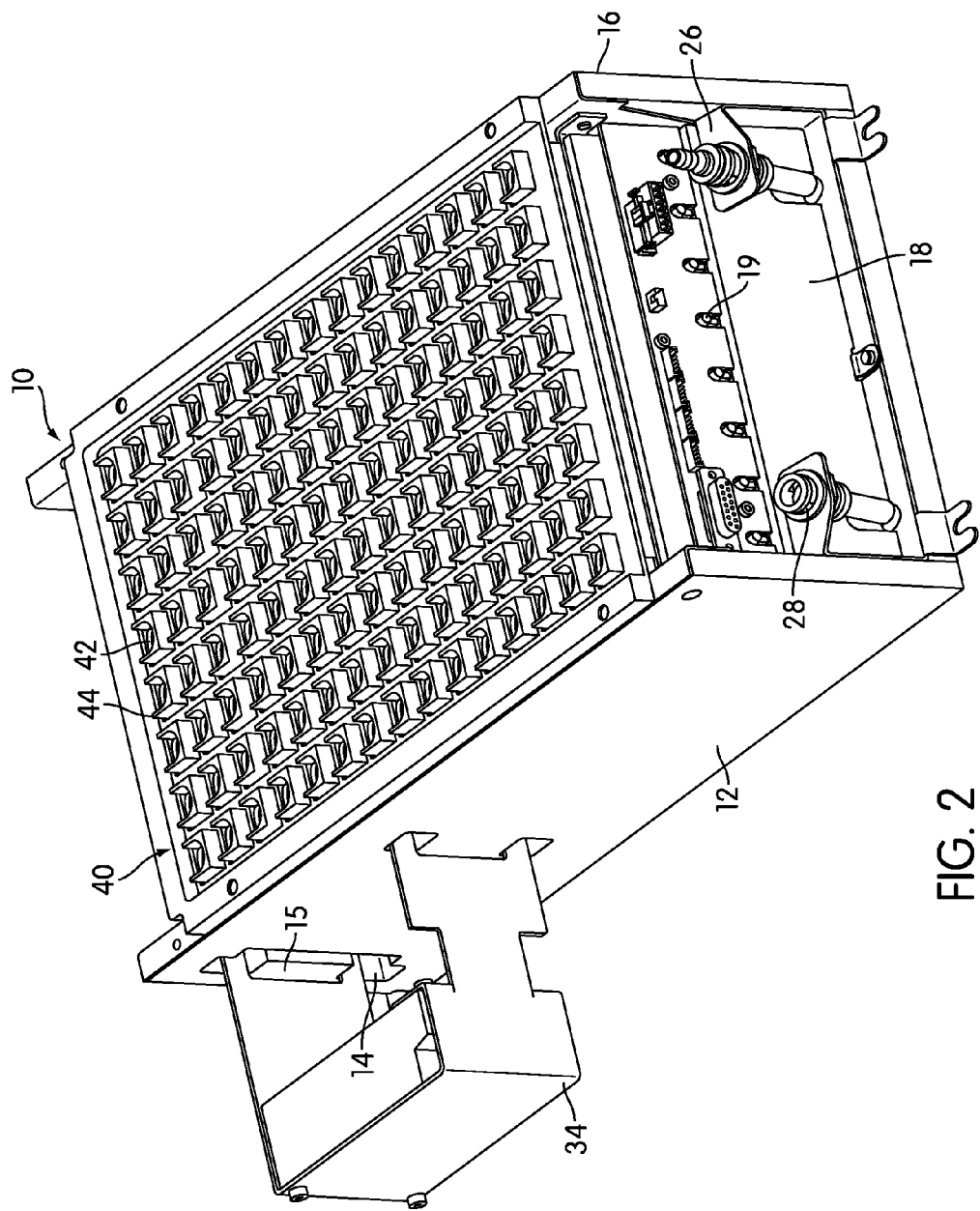
FIG. 2 is an upper rear perspective view of the sample receptacle module.
Figure 3:
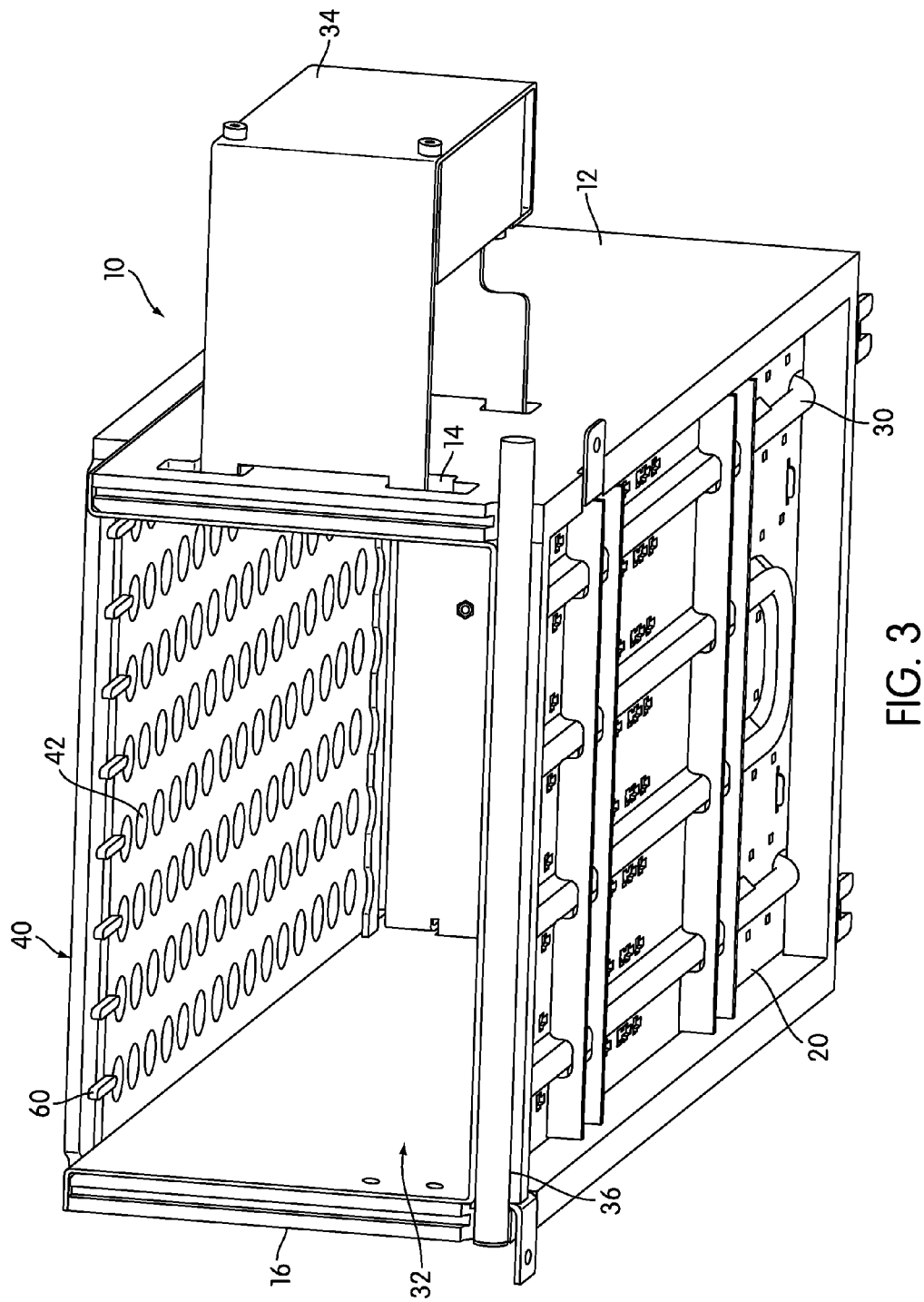
FIG. 3 is a lower front perspective view of a sample bay of the sample receptacle module.

As shown in FIGS. 1-3, the sample bay 10 is a box-like structure having a first side wall 12, a second side wall 16, a back wall 18, and a floor plate 20. The walls 12, 16, and 18 may be thermally insulated. The sample bay 10 further includes a sample bay cover 40 carried at its edges by the walls 12, 16, and 18. A front end 32 of the sample bay 10 is open to permit the sample racks 100 to be inserted into and removed from the sample bay 10. The floor plate 20 may further include sample rack guides 22 which engage mating guides formed in the bottom of each sample rack 100 for accurately and repeatably positioning each rack. Holes 19 formed in back wall 18 are aligned with each sample rack position.

Sample bay 10 further includes a barcode bracket 34 mounted to the first side wall 12 and configured to carry a barcode reader 15 in an operative position with respect to a barcode window 14 formed in the first side wall 12. The barcode reader 15 carried in the barcode bracket 34 is configured to read barcodes placed on individual sample receptacles carried in each of the sample racks 100 as well as barcodes on the sample racks 100 themselves. The barcodes are read through the barcode window 14 as the sample rack is pushed into or removed from the sample bay 10. A procedure for reading the barcodes on sample receptacles s will be described below.

The interior of the sample bay 10 is preferably kept at a cooler than ambient temperature by means of a coolant medium flowing through a coolant tube 30 arranged beneath the floor plate 20, as shown in FIG. 3. The coolant medium, which may comprise chilled water, is passed through the coolant tube 30 via a coolant inlet connector 28 and a coolant outlet connector 26 mounted behind the back wall 18, as shown in FIG. 2.

The chilled interior of the sample bay 10 can cause an accumulation of condensation inside the sample bay 10. To convey accumulated water away from the sample bay 10, a condensation tube 36 is provided along the lower front edge of the front opening 32. The condensation tube 36 includes a top longitudinal slot 38, and a front edge 24 of the floor plate 20 is bent into the slot 38 to direct excess condensation collected on the floor plate 20 into the condensation tube 36. Condensation tube 36 conveys the collected condensation to a remote container or drain (not shown).

The sample bay cover 40 has formed therein a plurality of sample receptacle access openings 42, which, in the illustrated embodiment, are arranged in a rectangular array of rows and columns, each column of openings aligning with the position of a sample rack 100. A raised element, referred to as a viscous string removal element 44, is provided adjacent each access opening 42. The function of the viscous string removal elements 44 will be described below.

The sample rack 100 is shown in further detail in FIGS. 4-7. Sample rack 100 is adapted to receive and hold a plurality of receptacles, which, in certain embodiments, may comprise tubular containers, such as test tubes. Sample rack 100 includes a receptacle holder 102 and a cover 130. The receptacle holder 102 includes a handle 104 for grasping and carrying the sample rack 102 and for inserting the receptacle holder 102 into or removing the receptacle holder 102 from the sample bay 10. In one embodiment, a machine-readable label, such as a barcode 103, is provided on the receptacle holder 102, such as near the handle 104 as shown.

The receptacle holder 102 may be made from a suitable, non-reactive material, such as plastic or Delrin® acetyl resin, and includes a base 106 extending longitudinally from the handle 104. A guide track 108 is formed in the base 106 for engaging the sample rack guides 22 provided in the floor plate 20 of the sample bay 10 to ensure proper positioning of the sample rack 100 within the sample bay 10. An alignment slot 118 is formed in a top edge above the handle 104. Alignment slot 118 engages one of the alignment projections 60 formed along the bottom of a front edge of the sample bay cover 40 (See FIG. 3). A plurality of vertically oriented divider walls 110 extend upwardly, at spaced intervals, from the base 106. The upper portions of the divider walls 110 are held in fixed relative positions by a side panel 122 extending longitudinally from the handle 104 to an end wall 120 along one side of the receptacle holder 102. The gap between each pair of adjacent divider walls 110 defines a sample receptacle pocket 124, or receptacle-receiving area, for receiving an individual receptacle. In one embodiment, pocket-identifying indicia, such as barcode 125, is provided on the divider walls 110 adjacent each pocket 124. The indicia, which may also include an alphanumeric identifier, "A", "B", "C", etc., uniquely identifies each pocket 124. A machine readable label, such as "empty pocket" barcode 123, may be provided within each pocket 124, on the inner side of surface panel 122 to uniquely identify each pocket and to indicate when a receptacle is not present in the pocket 124.

Figure 4:
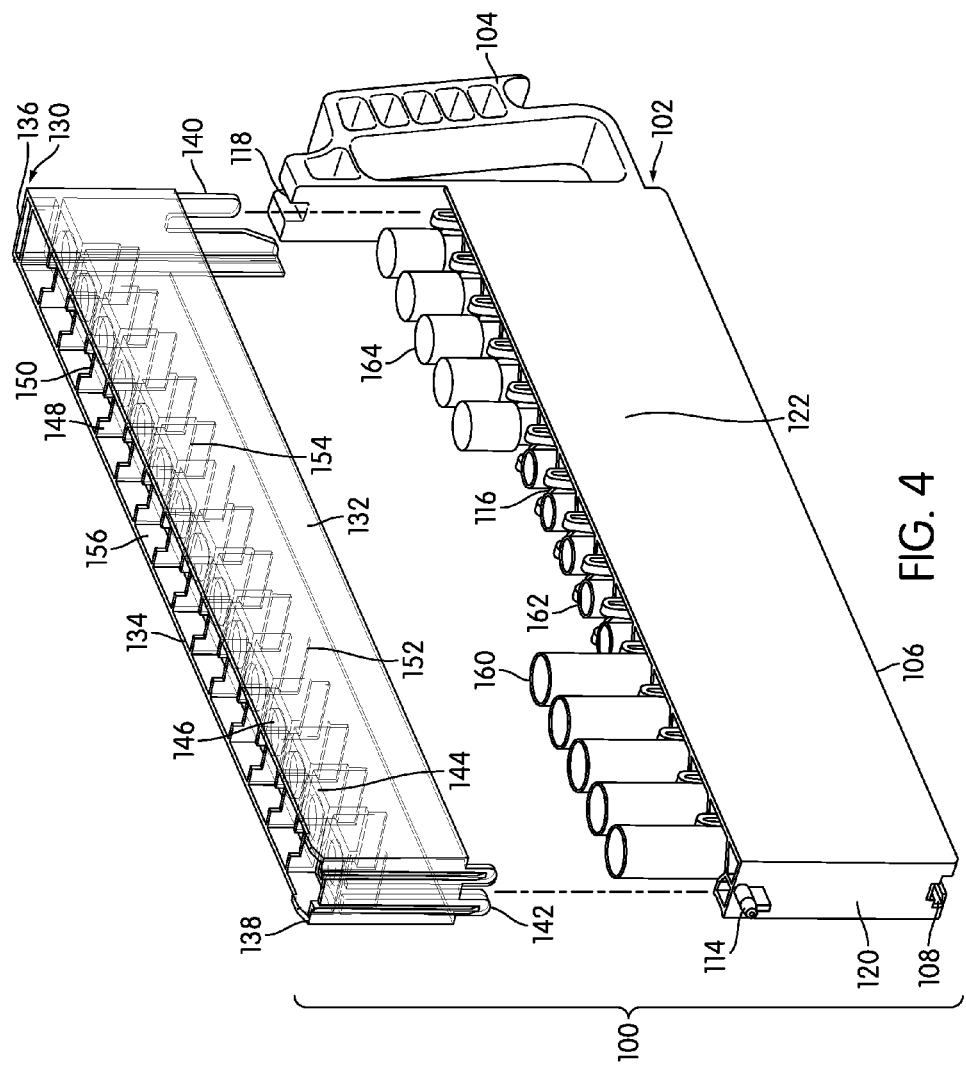
FIG. 4 is a perspective view of a sample rack of the sample receptacle module including a receptacle holder and a cover.
Figure 5:
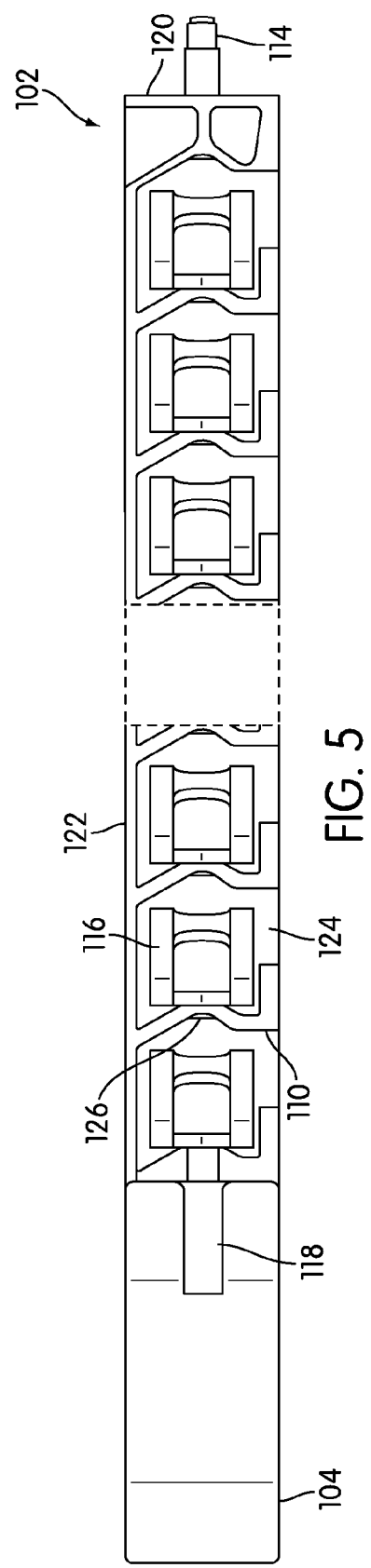
FIG. 5 is a top view of the receptacle holder with the cover removed.
Figure 6:
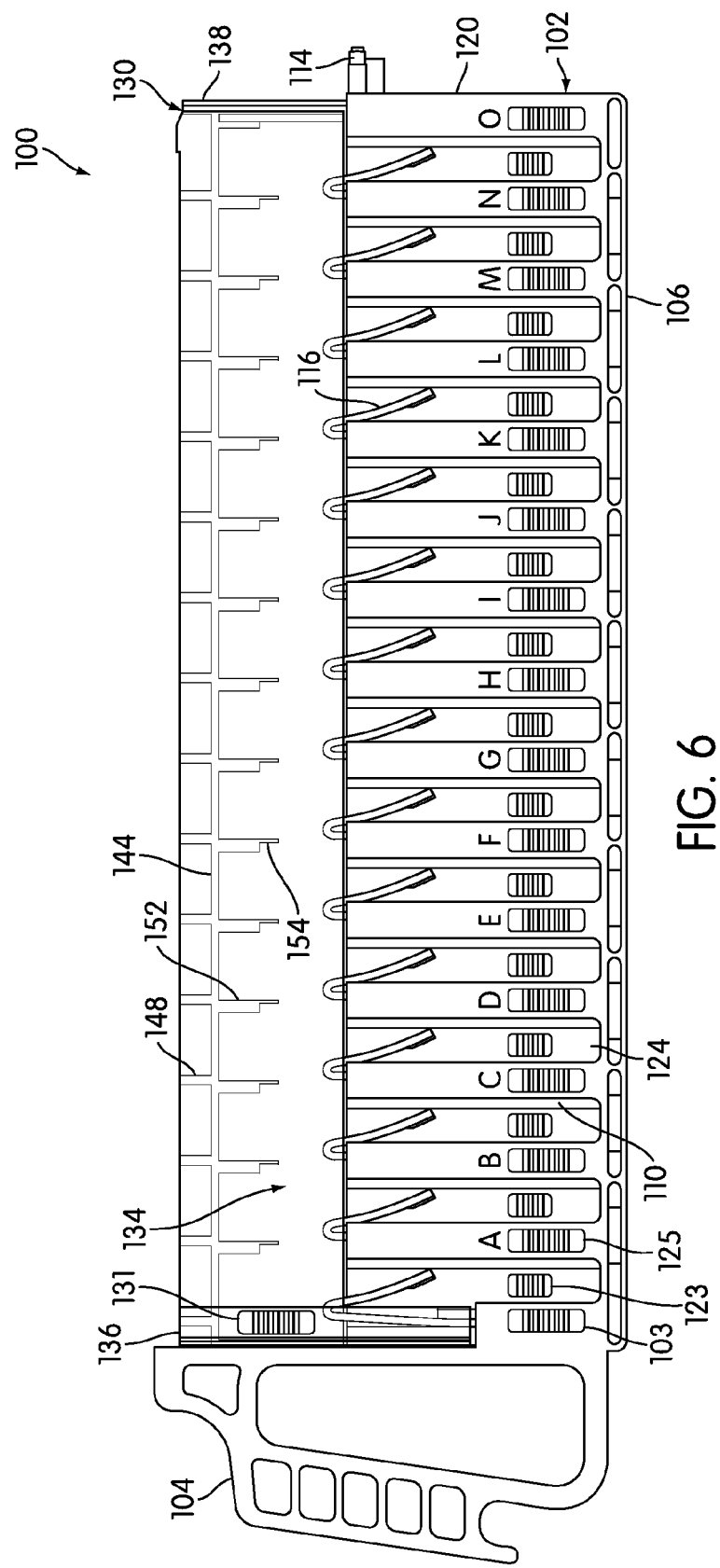
FIG. 6 is a side view of the sample rack, including the receptacle holder and the cover.
Figure 7:
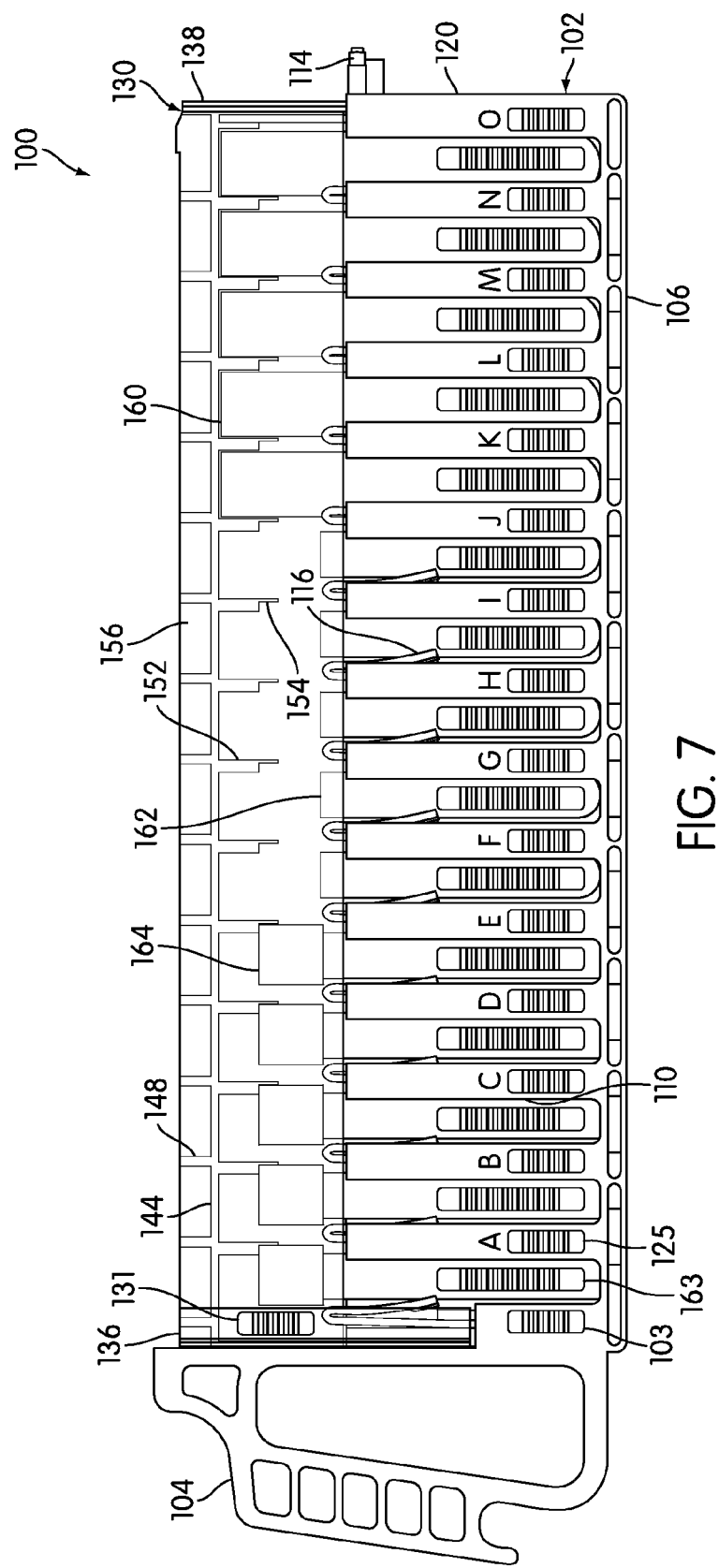
FIG. 7 is side view of the sample rack, including the receptacle holder and the cover, with a plurality of differently-sized sample receptacles carried in the receptacle holder.

A resilient element, such as a spring clip 116, is provided in each sample receptacle pocket 124. Spring clip 116 comprises a bent element (made of, e.g., spring stainless steel) with one portion attached to one divider wall 110 defining a receptacle pocket 124 and another portion extending at an acute angle into the pocket. Each sample receptacle pocket 124 can accommodate receptacles of varying sizes. The receptacle is held in a relatively secure, fixed position within the pocket 124 by means of the spring clip 116 which urges the receptacle toward a divider wall 110 forming one side of the sample receptacle pocket 124. As shown in FIG. 5, each divider wall 110 incorporates a positioning feature, such as a shallow V-shaped notch 126, which assists in positioning (e.g., centering) a receptacle urged against the divider wall 110 by the spring clip 116. FIGS. 4 and 7 show the receptacle holder 102 carrying a plurality of large receptacles 160, small receptacles 162, and medium-sized, capped receptacles 164. In one embodiment, the receptacles are test tubes ranging in size from 12 mm to 16 mm in diameter.

Cover 130 fits over the top ends of the sample receptacles projecting above the receptacle holder 102, and is preferably made from a transparent or translucent plastic material so that the contents of the receptacle holder 102 can be observed without removing the cover 130. The cover 130 includes first and second longitudinal side walls 132, 134 and end walls 136, 138. The cover 130 may include structural elements for realeasably securing the cover 130 to the receptacle holder 102. In the illustrated embodiment, the cover includes locking forks 140, 142 at opposite ends of the cover 130 (See FIG. 4) which engage mating elements (not shown) formed in the receptacle holder 102 for realeasably securing the cover 130 to the receptacle holder 102. In one embodiment, cover 130 includes a machine-readable label, such as barcode 131.

A horizontal transverse wall 144 extends between the side and end walls 132, 134, 136, 138 below the topmost edges of the side and end walls, thereby defining a trough 156 in the upper portion of the cover 130. A plurality of longitudinally-spaced access openings 146 are formed in the transverse wall 144 and upper divider walls 148 extend laterally between the side walls 132, 134 between each of the access openings 146. Each upper divider wall 148 includes a rectangular notch 150 formed in an upper, central portion thereof. Lower divider walls 152 extend laterally between the side walls 132, 134 below the transverse wall 144 at positions between the access openings 146. The space between consecutive lower divider walls 152 is large enough to accommodate the width (e.g., diameter) of the largest receptacle that can be carried in a sample receptacle pocket 124 (see large tubes 160 in FIG. 7). The cover 130 further includes a receptacle-retaining element configured to engage a portion of the top of certain-sized receptacles urged into a centered, or other predetermined, position within each receptacle pocket 124 by the spring clip 116 and the V-shaped notch 126. More specifically, in the illustrated embodiment, each lower divider wall 152 includes a cap notch 154 extending across the divider wall 152 at a lower end thereof. The cap notch 154 accommodates a receptacle cap when the cover 130 is placed over a receptacle holder 102 carrying one or more capped receptacles 164 (see FIG. 7).

Capped receptacles 164 may comprise receptacles provided with a cap that is penetrable by the probe of a fluid transfer mechanism, such as described in U.S. Pat. Nos. 6,893,612 or 7,435,389. The probe penetrates the cap by puncturing one or more piercable members of the cap as the probe is moved into the receptacle. The cap may also include a filter element through which the probe must pass before reaching a fluid contained within the receptacle 164. After the probe penetrates the cap, friction between the penetrated portions of the cap and/or the filter element and the probe can cause the receptacle 164 to lift out of its pocket when the probe is withdrawn from the receptacle 164. The cap notch 154 of the cover 130 applies a downward holding force on the capped receptacle 164 to prevent the receptacle 164 from being lifted out of the receptacle pocket 124 when a probe that has penetrated the cap is withdrawn from the receptacle 164.

A home pin 114 extends from the end wall 120. Home pin 114 lets the instrument know that the sample rack has been fully inserted into the sample bay 10, or when it is being removed, for example by extending through holes 19 formed in back wall 18 and engaging a sensor, such as a slotted optical sensor (not shown) mounted to the back wall 18. Home pin 114 may also function as a positioning element to assure the rack is absolutely vertical.

The sample rack 100 is placed within the sample bay 10 by positioning the sample rack 100 in an aligned orientation with respect to the sample rack guides 22 provided on the floor plate 20 of the sample bay 10. As noted, sensors may be provided for detecting the presence of a sample rack 100 and to indicate whether the sample rack 100 is fully inserted into the sample bay 10.

Receptacles are placed in the sample rack so that machine-readable labels (e.g., barcodes 163, see FIG. 7) as well as human-readable labels are visible through the side opening of each pocket 124 between adjacent divider walls 110. As a sample rack 100 is inserted into the sample bay 10, the barcode reader 15 reads each barcode 163 sequentially as the receptacles 160, 162, and/or 164 carried in the receptacle holder 102 pass the barcode window 14. If a pocket 124 is empty, the barcode 123 is read, indicating the absence of a receptacle in the pocket 124. Each pocket-identifying barcode 125 is also read by the barcode reader 15 to provide pocket identification data with which to associate the receptacle (or absence of a receptacle) carried in the corresponding pocket 124. Preferably only one barcode reader is provided and, therefore, as can be appreciated from FIG. 1, it will be necessary to fill sample rack lanes (defined by the sample rack guides 22) moving from left to right so that there is no carrier between the carrier being inserted and the barcode window 14 and barcode reader 15. Indicator lights at each of the lanes may illuminate sequentially as an indication to the operator as to which lane should be loaded next. The barcode information for each receptacle is stored (e.g., in the memory of an instrument computer controller (not shown)), and that information is correlated with the carrier position (i.e., lane) within the sample bay 10. The barcode reader also reads the sample holder barcode 103 to identify the holder 102 and the cover bar code 131 to ensure that the cover 130 is in place.

Occasionally, receptacles are labeled with barcodes of relatively poor quality that can be read only by a barcode reader that is in relatively close proximity to the barcodes. For such situations, the sample bay 10 and instrument controller preferable provide a "high resolution reading mode" ("HRM"), referred to as the high resolution reading mode because it is in this mode in which the barcode reader 15 can read in the highest resolution (i.e., smallest line size). HRM is preferably operator-selectable. After HRM is selected, the sample rack 100 loaded with receptacles 160, 162, and/or 164 with barcodes 163 is first inserted in the far right-hand sample rack lane, closest to the barcode reader 15 and window 14 (this will be referred to as the high resolution reading lane). An audible and/or visible indicator may be provided to identify the high resolution reading lane. As the sample rack 100 is inserted into the high resolution reading lane, each receptacle barcode 163 is read and receptacle data obtained by reading the barcode 163 is stored. Pocket-identifier barcodes 125 and a rack identifier barcode 102 are read and stored as well. The pocket-identifier data and the rack-identifier data are associated with the receptacle data obtained for each of the receptacles in the rack, for example in a relational database. The close proximity of the high resolution reading lane to the barcode reader 15 will increase the likelihood of an accurate read. After the sample rack 100 has been fully inserted into the high resolution reading lane, the sample rack 100 is then withdrawn. A sensor may be provided to sense when the sample rack 100 has been fully inserted, and an indicator light and/or audible tone may signal to the operator that the sample rack 100 may be removed. After the sample rack 100 is removed, it is then re-inserted into one of the other, available lanes. An indicator light may be provided to identify the lane into which the sample rack 100 is to be inserted. As the sample rack 100 is inserted into the available lane, the barcodes 163 on the receptacles are not re-read, but the sample rack identifier barcode 103 is read to confirm that the sample rack 100 that was just scanned in the high resolution reading lane is being inserted. The cover barcode 131 may also be read to ensure the positioning of the cover 130. The receptacle data associated in the database with that rack identification then becomes associated with that lane. The controller may be configured to erase or otherwise disable the barcodes if the sample rack 100 is not re-inserted into an available lane within a specified period of time (e.g., 5 seconds). Thus, if the sample rack 100 is not re-inserted into the sample bay 10 within the specified period of time, the controller will not recognize the sample rack 100 as having been previously scanned in the high resolution reading lane, and the sample rack 100 will have to be scanned in the high resolution reading lane again. This control feature will minimize the ability to switch one or more un-scanned receptacles for scanned receptacles in the time between withdrawing the sample rack 100 from the high resolution reading lane and reinserting the sample rack 100 into another available lane.

After the sample rack 100 is inserted into the sample bay 10, sample material contained in receptacles carried in the sample rack 100 can be accessed via a fluid transfer mechanism—such as the probe (e.g., a barrel with a protective tip, such as a pipette tip, mounted thereon) of an automated, robotically operated pipetting device—through the access openings 42 formed in the sample bay cover 40 and the access openings 146 formed in the cover 130. Sample material may include, for example, urine, blood, plasma, saliva, mucus, seminal fluid, amniotic fluid, cerebrospinal fluid, synovial fluid, cultures, and the like. When a probe of a pipetting device is submerged in a viscous sample material carried in a receptacle and then withdrawn, a viscous string of the sample material may result in a string of viscous material being suspended from a distal end of the probe after the probe is withdrawn from the sample receptacle. Further movement of the sample transfer probe may drag the string of viscous material along with it, thereby potentially causing cross-contamination should a portion of the string of viscous material fall into another sample receptacle or a reaction receptacle or contact a contamination sensitive surface or component. Accordingly, the sample bay cover 40 includes viscous string removal elements 44 adjacent to each sample receptacle access opening 42, and relative movement of the sample transfer probe in a prescribed manner with respect to the viscous string removal element will remove the string of viscous material in a controlled manner at a known location and in such a way as to prevent the string of viscous material from falling into another sample receptacle.

Figure 8:
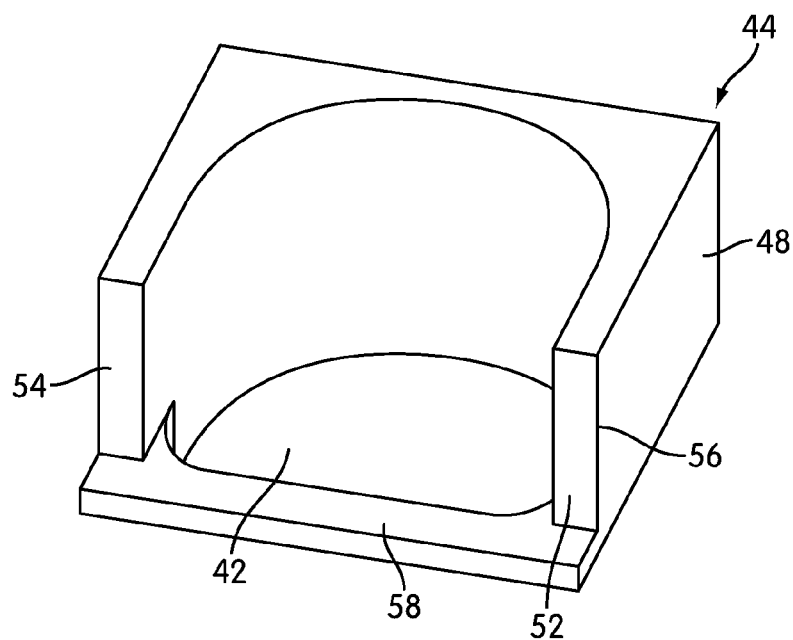
FIG. 8 is an enlarged upper front perspective view showing, in isolation, a single viscous string removal element of the sample bay cover of FIGS. 1 and 2.
Figure 9:
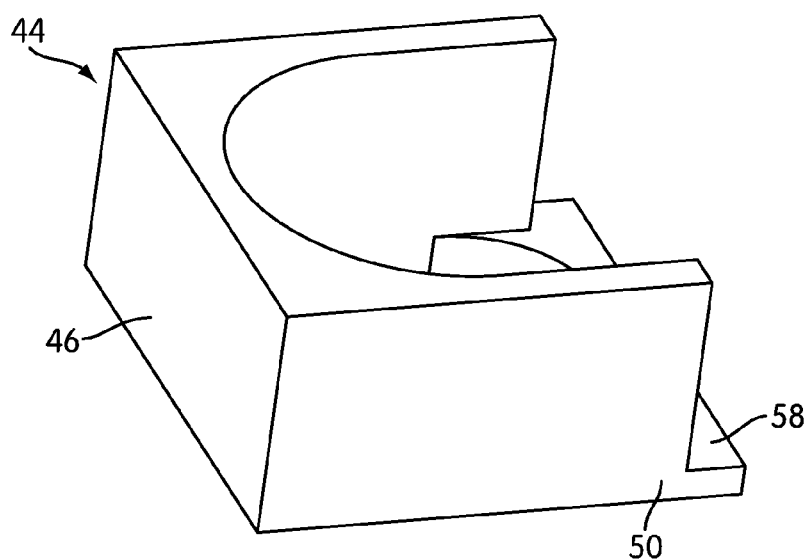
FIG. 9 is a rear upper perspective view showing, in isolation, the viscous string removal element of FIG. 8.

Details of the viscous string removal element 44 are shown in FIGS. 8 and 9. According to one embodiment, the viscous string removal element 44 comprises a generally square, U-shaped raised element at least partially surrounding each sample receptacle access opening 42. The element 44 includes side surfaces 48, 50 and a back surface 46 that surround the access opening 42 on three sides. End surfaces 52, 54 are located on either side of the open end of the U-shaped element, and a corner 56 defines a transition, or edge, between the side surface 48 and one of the end surfaces 52. A raised ledge 58 extends adjacent to the access opening 42 across the open end of the U-shaped element 44. Corner 56 is set back from the edge of raised ledge 58 to allow more room for the pipettor to travel between adjacent U-shaped elements. In one embodiment the removal element 44 is 17 mm wide, 17 mm long, 8 mm high, with the raised ledge 58 that is 1 mm high. The opening 42 is 13.8 mm in diameter. The gap width between side-by-side adjacent removal elements 44 is 8 mm, while the gap between lengthwise adjacent removal elements 44 is 5 mm. The raised edge 58 has a length (or depth) of 2 mm, so the distance between the back surface 46 of one element 44 and the end surfaces 52, 54 is 7 mm.

Figure 10:
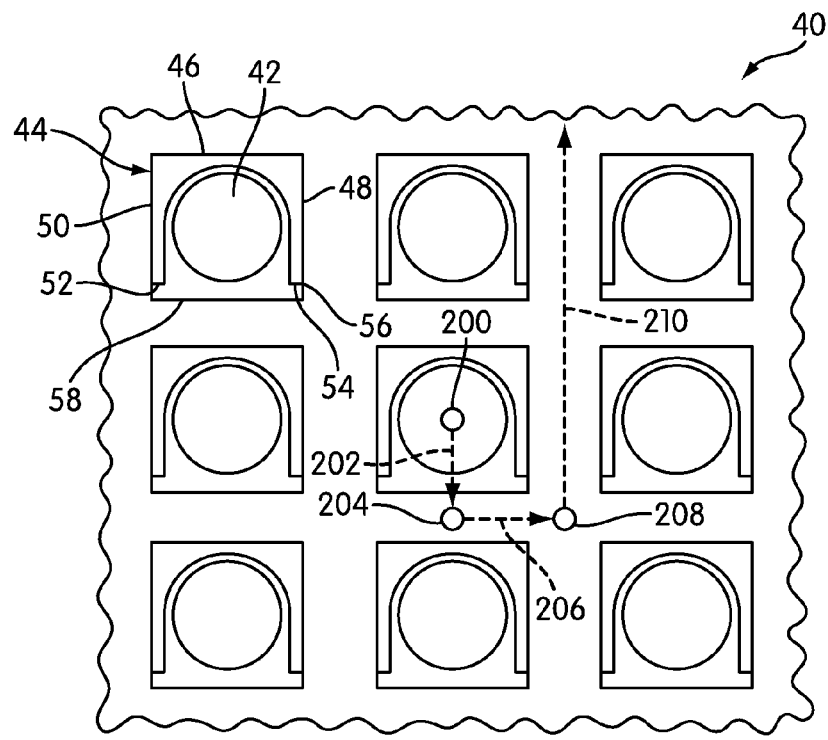
FIG. 10 is a partial top view of the sample bay cover of FIGS. 1 and 2 showing viscous string removal elements and schematically indicating a path traveled by a sample transfer probe while moving from a sample access opening formed in the cover.

The manner in which the viscous string removal elements 44 are used to remove a string of viscous material suspended from a probe will be described with reference to FIG. 10. As shown in FIG. 10, which shows a portion of the sample bay cover 40, the probe is at position 200 when it is first withdrawn from the sample receptacle access opening 42. The probe is then moved with respect to the access opening 42 and the element 44 along a path that includes a first segment 202 to a position 204 that is offset from (i.e., not aligned with) the access opening 42. The path of the probe next includes a second leg 206 to a third position 208 and then a third leg 210 between adjacent rows of removal elements 44. Note that after moving from position 200 to position 204 offset from the access opening 42, the probe does not again move over any other access opening in the cover 40.

While the probe moves along the path encompassing segments 202, 206, and 210, any string of viscous material suspended from the probe will be dragged behind the probe (relative to the direction of probe movement) and extend in a direction generally opposite the direction of movement of the probe. A change in direction of the probe caused by the transition from second leg 206 to third leg 210 will cause the string suspended from the probe to contact the corner 56 of the element 44. Corner 56 preferably defines a relatively sharp edge that will create friction between corner 56 and the string of viscous material as the probe continues to move relative to the corner 56. Thus, further movement of the probe along the third leg 210 of the path, combined with the friction between the string of viscous material and the corner 56, will cause the string of viscous material to be separated from the probe. The raised ledge 58 provides an obstruction that will impede any material falling from the probe onto the cover 40 from flowing back into an access opening 42.

Figure 11:
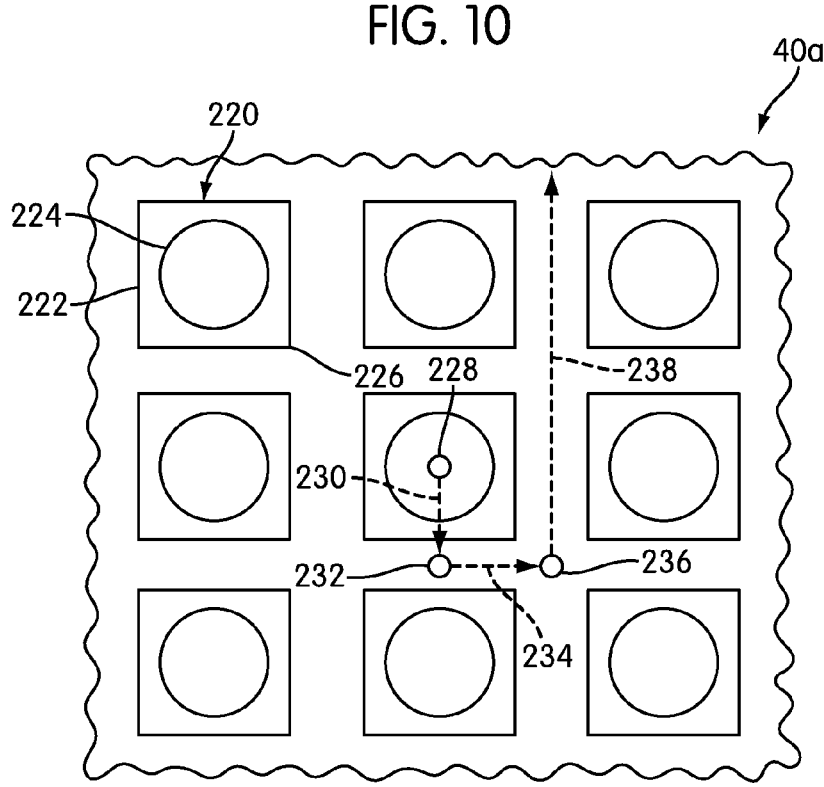
FIG. 11 is a partial top view of a sample bay cover showing a first alternative configuration of viscous string removal elements and schematically indicating a path traveled by a sample transfer probe while moving from a sample access opening formed in the cover.

Details of a first alternative embodiment of a viscous string removal element are shown in FIG. 11, which shows part of alternative embodiment of a sample bay cover 40a. The viscous string removal element, designated by reference number 220, comprises a generally square raised element surrounding each sample receptacle access opening 224. The element 220 includes four side surfaces 222 that surround the access opening 224 on four sides. Corners 226 define transitions, or edges, between side surfaces 222.

Referring to FIG. 11, the probe is at position 228 when it is first withdrawn from the sample receptacle access opening 224. The probe is then moved with respect to the access opening 224 and the element 220 along a path that includes a first segment 230 to a position 232 that is offset from the access opening 224. At position 232, the probe may be lowered so that the lowest end of the probe (the distal end of the probe) is below the top of the element 220. The path of the probe movement next includes a second leg 234 to a third position 236, and then a third leg 238 between adjacent rows of removal elements 220. The path of the probe avoids taking the probe over any other access opening 224 in the cover 40a.

Again, as the probe moves, any string of viscous material suspended from the probe will be dragged behind the probe (relative to the direction of probe movement) and extend in a direction generally opposite the direction of movement of the probe. A change in direction of the probe caused by the transition from second leg 234 to third leg 238 will cause the string suspended from the probe to contact the corner 226 of the element 220. Corner 226 preferably defines a relatively sharp edge that will create friction between corner 226 and the string of viscous material as the probe continues to move relative to the corner 226. Thus, further movement of the probe along the third leg 238 of the path, combined with the friction between the string of viscous material and the corner 226, will cause the string of viscous material to be separated from the probe. As can be appreciated from FIG. 11, the aligned viscous string removal elements 44 form a lane (corresponding to the direction of leg 238) with nearly-continuous walls on opposite sides thereof defined by the facing sides 222 of adjacent removal elements 44. The probe can move through this lane, with its distal tip located below the tops of the elements 44, and any material released from a distal end of the probe would be prevented from entering into the other openings. Thus, the walls 222 provide an edge 226 to break strings of viscous material and also provide a shield against drips or flinging droplets.

Figure 12:
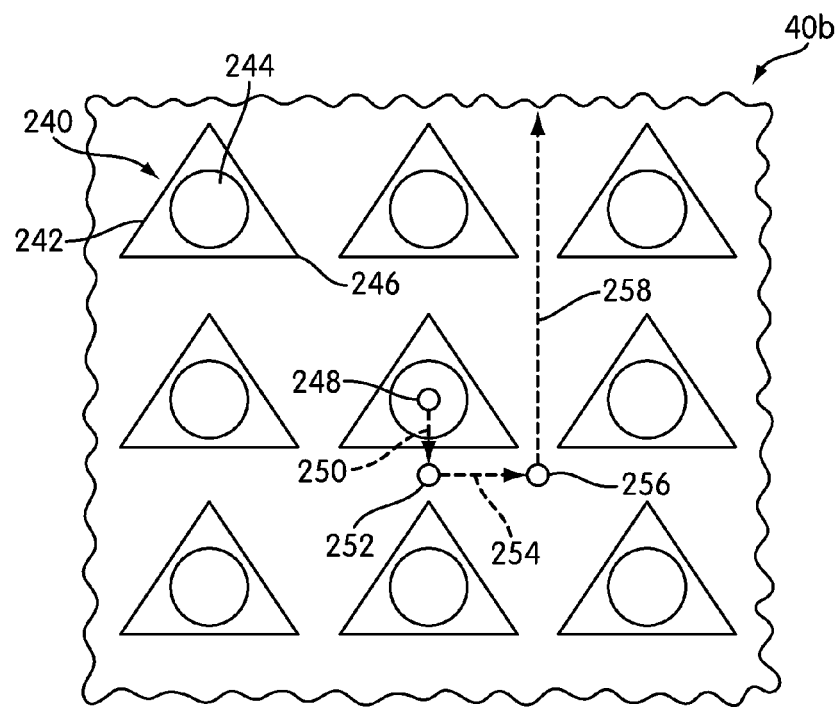
FIG. 12 is a partial top view of a sample bay cover showing a second alternative configuration of viscous string removal elements and schematically indicating a path traveled by a sample transfer probe while moving from a sample access opening formed in the cover.

Details of a second alternative embodiment of a viscous string removal element are shown in FIG. 12, which shows part of alternative embodiment of a sample bay cover 40b. The viscous string removal element, designated by reference number 240, comprises a generally triangular raised element surrounding each sample receptacle access opening 244. Removal element 240 includes three side surfaces 242 that surround the access opening 244. Corners 246 define transitions, or edges, between side surfaces 242.

Referring to FIG. 12, the probe is at position 248 when it is first withdrawn from the sample receptacle access opening 244. The probe is then moved with respect to the access opening 244 and removal element 240 along a path that includes a first segment 250 to a position 252 that is offset from the access opening 244. At position 252, the probe may be lowered so that the lowest end of the probe is below the top of removal element 240. The path of the probe next includes a second leg 254 to a third position 256, and then a third leg 258 between adjacent rows of removal elements 240. The path of the probe avoids taking the probe over any other access opening 244 in the cover 40b.

Again, as the probe moves, any string of viscous material suspended from the probe will be dragged behind the probe (relative to the direction of probe movement) and extend in a direction generally opposite the direction of movement of the probe. A change in direction of the probe caused by the transition from second leg 254 to third leg 258 will cause the string suspended from the probe to contact the corner 246 of removal element 240. Corner 246 preferably defines a relatively sharp edge that will create friction between corner 246 and the string of viscous material as the probe continues to move relative to the corner 246. Thus, further movement of the probe along the third leg 258 of the path, combined with the friction between the string of viscous material and the corner 246, will cause the string of viscous material to be separated from the probe.

Figure 13:
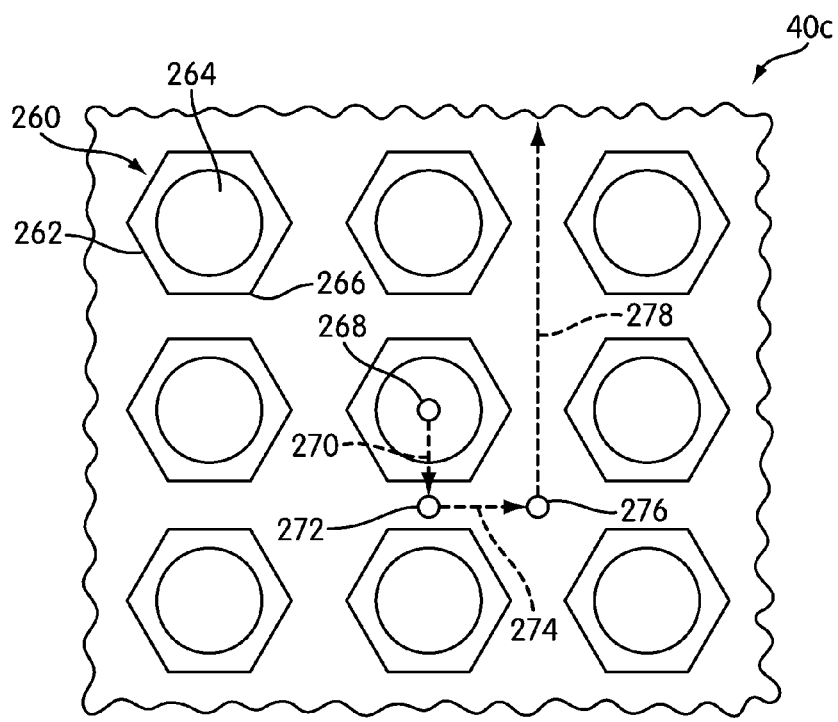
FIG. 13 is a partial top view of a sample bay cover showing a third alternative configuration of viscous string removal elements and schematically indicating a path traveled by a sample transfer probe while moving from a sample access opening formed in the cover.

Details of a third alternative embodiment of a viscous string removal element are shown in FIG. 13, which shows part of alternative embodiment of a sample bay cover 40c. The viscous string removal element, designated by reference number 260, comprises a raised element in the shape of a hexagon surrounding each sample receptacle access opening 264. Removal element 260 includes six side surfaces 262 that surround the access opening 264. Corners 266 define transitions, or edges, between the side surfaces 262.

Referring to FIG. 13, the probe is at position 268 when it is first withdrawn from the sample receptacle access opening 264. The probe is then moved with respect to the access opening 264 and removal element 260 along a path that includes a first segment 270 to a position 272 that is offset from the access opening 264. At position 272, the probe may be lowered so that the lowest end of the probe is below the top of removal element 260. The path of the probe next includes a second leg 274 to a third position 276, and then a third leg 278 between adjacent rows of removal elements 260. The path of the probe avoids taking the probe over any other access opening 264 in the cover 40c.

Again, as the probe moves, any string of viscous material suspended from the probe will be dragged behind the probe (relative to the direction of probe movement) and extend in a direction generally opposite the direction of movement of the probe. A change in direction of the probe caused by the transition from second leg 274 to third leg 278 will cause the string suspended from the probe to contact the corner 266 of removal element 260. Corner 266 preferably defines a relatively sharp edge that will create friction between corner 266 and the string of viscous material as the probe continues to move relative to the corner 266. Thus, further movement of the probe along the third leg 278 of the path, combined with the friction between the string of viscous material and the corner 266, will cause the string of viscous material to be separated from the probe.

Figure 14:
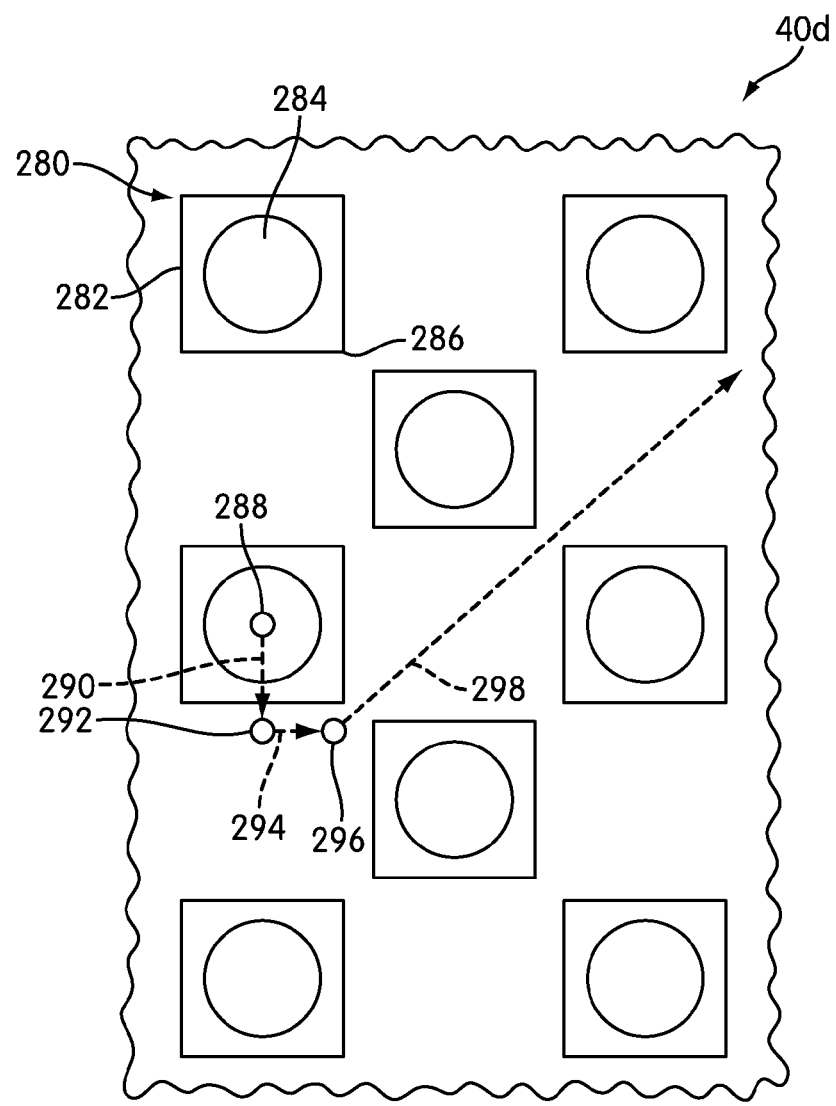
FIG. 14 is a partial top view of a sample bay cover showing a fourth alternative configuration of viscous string removal elements and schematically indicating a path traveled by a sample transfer probe while moving from a sample access opening formed in the cover.

Details of a fourth alternative embodiment of a viscous string removal element are shown in FIG. 14, which shows part of alternative embodiment of a sample bay cover 40d. The viscous string removal element, designated by reference number 280, comprises a generally square raised element surrounding each sample receptacle access opening 284. Removal element 280 includes four side surfaces 282 that surround the access opening 284 on four sides. Corners 286 define transitions, or edges, between the side surfaces 282. Sample bay cover 40d differs from sample bay cover 40a, which also includes square viscous string removal elements 220 (See FIG. 11), in that the adjacent rows of removal elements 280 of sample bay cover 40d are offset from each other.

Referring to FIG. 14, the probe is at position 288 when it is first withdrawn from the sample receptacle access opening 284. The probe is then moved with respect to the access opening 284 and removal element 280 along a path that includes a first segment 290 to a position 292 that is offset from the access opening 284. At position 292, the probe may be lowered so that the lowest end of the probe is below the top of removal element 280. The path of the probe next includes a second leg 294 to a third position 296, and then a third leg 298 in a diagonal direction between diagonally adjacent removal elements 280. The path of the probe avoids taking the probe over any other access opening 284 in the cover 40d.

Again, as the probe moves, any string of viscous material suspended from the probe will be dragged behind the probe (relative to the direction of probe movement) and extend in a direction generally opposite the direction of movement of the probe. A change in direction of the probe caused by the transition from second leg 294 to third leg 298 can cause the string suspended from the probe to contact the corner 286 of removal element 280, even if that transition does not encompass a 90 degree change in direction as shown in FIGS. 10-13. Thus, further movement of the probe along the third leg 298 of the path, combined with the friction between the string of viscous material and the corner 286, will cause the string of viscous material to be separated from the probe.

Figure 15:
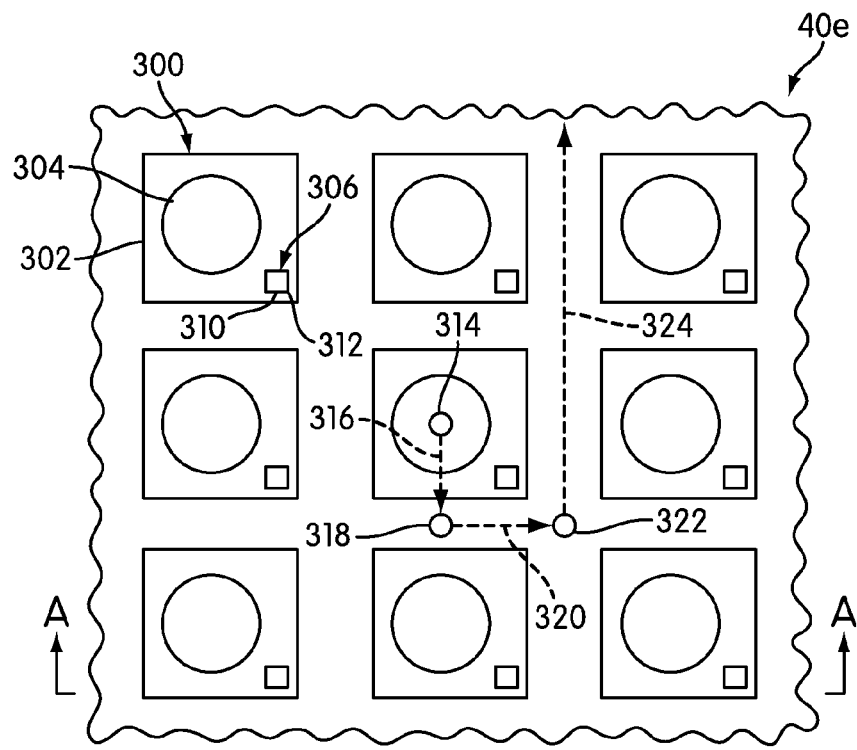
FIG. 15 is a partial top view of a sample bay cover showing a fifth alternative configuration of viscous string removal elements and schematically indicating a path traveled by a sample transfer probe while moving from a sample access opening formed in the cover.
Figure 15A:
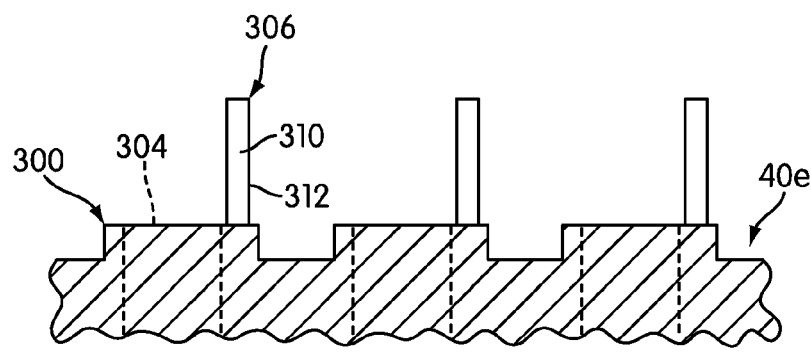
FIG. 15A is a cross-section along line A-A in FIG. 15.

Details of a fifth alternative embodiment of a viscous string removal element are shown in FIGS. 15 and 15A, which show part of alternative embodiment of a sample bay cover 40e. The viscous string removal element, designated by reference number 300, comprises a raised surface 302 surrounding each sample receptacle access opening 304 and a post 306 projecting above the raised surface 302. Post 306 includes side surfaces 310 (four sides 310 in the illustrated embodiment) and corners 312 which define transitions, or edges, between the side surfaces 310. Post 306 may have any other shape that will provide an edge between non-coplanar sides of the post, such as triangular or hexagonal, in addition to square or rectangular. The post 306 may be positioned on the raised surface 302 so that one corner edge 312 of post 306 coincides with a corner edge of the raised surface 302 (not shown). On the other hand, raised surface 302 may have any shape, including shapes, such as circular, not defining corner edges.

Referring to FIG. 15, the probe is at position 314 when it is first withdrawn from the sample receptacle access opening 304. The probe is then moved with respect to the access opening 304 and removal element 300 along a path that includes a first segment 316 to a position 318 that is offset from the access opening 304. As can be appreciated from FIG. 15A, raised surface 302 is a shorter structure than post 306, and thus, it is not necessary to lower the probe at position 318, as the lower end of the probe will already be below the top of post 306. The path of the probe next includes a second leg 320 to a third position 322, and then a third leg 324 between adjacent rows of removal elements 300. The path of the probe avoids taking the probe over any other access opening 304 in the cover 40e.

Again, as the probe moves, any string of viscous material suspended from the probe will be dragged behind the probe (relative to the direction of probe movement) and extend in a direction generally opposite the direction of movement of the probe. A change in direction of the probe caused by the transition from second leg 320 to third leg 324 will cause the string suspended from the probe to contact the corner edge 312 of the post 306. Corner 312 preferably defines a relatively sharp edge that will create friction between corner 312 and the string of viscous material as the probe continues to move relative to the corner 312. Alternatively, post 306 may be of a shape that is devoid of corner edges, such as cylindrical, in which case, the necessary friction—should the cylindrical surface itself not provide sufficient friction—can be created by knurling, flutes or other surface modifications that will increase the friction of the exterior surface of the post. Thus, further movement of the probe along the third leg 324 of the path, combined with the friction between the string of viscous material and the post 306, will cause the string of viscous material to be separated from the probe. The raised surface 302 provides an obstruction that will impede any material falling from the probe onto the cover 40e from flowing back into an access opening 304.

Figure 16:
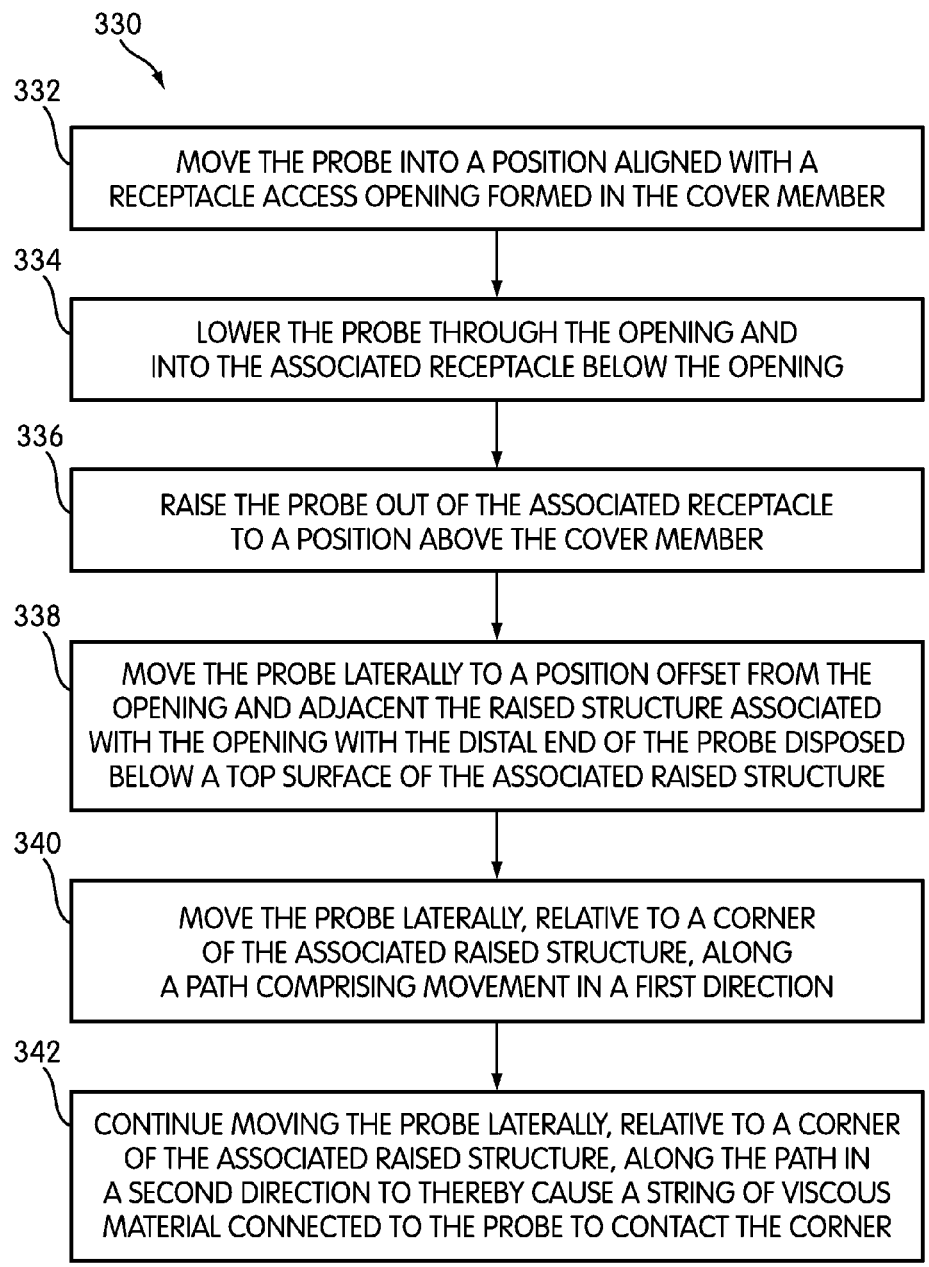
FIG. 16 is a flow chart illustrating a method for separating a string of viscous material from the probe of a fluid transfer mechanism.

FIG. 16 is a flow chart showing a method 330 for removing a string of viscous material from the probe of a fluid transfer mechanism. Method 330 is generally applicable to any of the embodiments shown in FIGS. 10-15. In step 332, the probe is moved into a position aligned with a receptacle access opening formed in the cover member. In step 334, the probe is lowered through the opening and into the associated receptacle located below the opening so that at least the distal end of the probe is submerged below the surface of the fluid contents of the receptacle. In step 336, the probe is raised out of the associated receptacle to a position above the cover member. In step 338, the probe is moved laterally to a position offset from the opening and adjacent the raised structure associated with the opening with the distal end of the probe disposed below a top surface of the associated raised structure. In step 340, the probe is moved laterally, relative to a corner of the associated raised structure, along a path comprising movement in a first direction. And in step 342, lateral movement of the probe, relative to a corner of the associated raised structure, is continued along the path in a second direction to thereby cause a string of viscous material connected to the probe to contact the corner.

Figure 17:
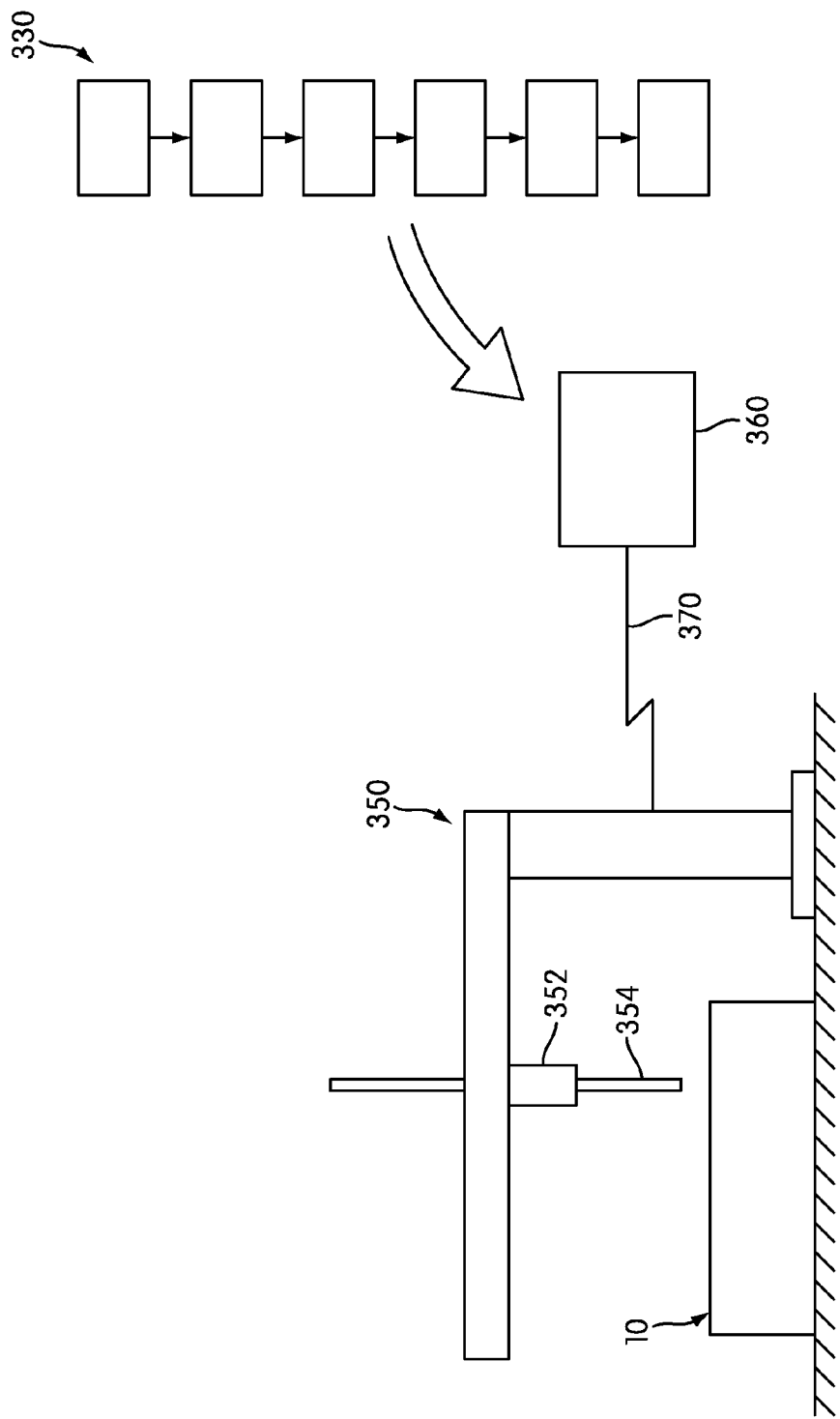
FIG. 17 is a schematic view of a system including a sample receptacle module, an automated pipettor, and a controller for controlling operation of the pipettor and programmed to execute an algorithm to cause the pipettor to perform the method illustrated in FIG. 16.

FIG. 17 is a schematic view of a system including a sample receptacle module 10, an automated pipettor 350, and a controller 360 for controlling operation of the pipettor 350. The automated pipettor includes a probe comprising a barrel 352 on which is mounted (e.g., frictionally) a protective tip 354 and is constructed and arranged to effect movement of the protective tip 354, for example, X-Y-Z movement (and, optionally, rotational movement about one or more axes). Automated pipettor 350 may include, or be connected to, a pump or other vacuum source (not shown), such as a syringe pump (e.g., the Cavro XP 3000), for effecting suction at the protective tip 354 for drawing fluid material into the protective tip 354. A suitable pipettor is disclosed in U.S. Patent Application Publication No. US 2008-0019878 A1. Suitable protective tips include pipette tips manufactured and sold by TECAN (TECAN U.S. Inc., Research Triangle Park, N.C.) under the trade name "Disposable Tips for GENESIS Series". In one embodiment, each tip has a 1000 μl capacity and is conductive. Controller 360 communicates with the automated pipettor via communication link 370 and may comprise a computer processor programmed to execute an algorithm (e.g., the algorithm represented by method 330 shown in FIG. 16 and described above) to control movement and operation of the pipettor.

The automated pipettor 350 may include a "self-teach" positioning capability. Position locator elements may be provided on the sample bay 10. During a self-teach procedure, the pipettor moves until it locates the position locator elements, and the coordinates of the position locator elements are stored in the controller 360. The positions of each of the access openings 42 and viscous string removal elements (e.g., removal elements 44) of the sample bay cover 40 relative to the positions of the position locator elements are known. Therefore, one the coordinates of the position locator elements are known, the coordinates of each of the access openings 42 and removal elements 44 are known as well.

The position locator elements may comprises locator pins (not shown) or other projections extending upwardly from the cover 40. Contact of the protective tip 354 with the locator pins can be detected by capacitive sensing or by force detection. Preferably two position locator elements are provided at separated positions on the sample bay 10 to facilitate determination of the location of the sample bay 10 and whether the sample bay 10 is skewed with respect to the orientation of the automated pipettor 350. Alternative position locator elements may comprise hall effect sensors or slotted optical detectors.

While the present invention has been described and shown in considerable detail with reference to certain illustrative embodiments, those skilled in the art will readily appreciate other embodiments of the present invention. Accordingly, the present invention is deemed to include all modifications and variations encompassed within the spirit and scope of the following appended claims.

The invention claimed is:

1. An apparatus for reading machine-readable labels disposed on receptacles and associating receptacle data read from each machine-readable label with a location within the system, said apparatus comprising:
   a plurality of rack-receiving locations, each configured to receive a rack holding at least one receptacle;
   a label reading device configured to read a rack-identifying machine-readable label disposed on the rack and a machine-readable label disposed on the at least one receptacle held on the rack, wherein said label reading device is disposed adjacent to one of said rack-receiving locations; and
   a data processing system, which includes data storage media and is configured to:
      read the machine-readable label of each receptacle having a machine-readable label and read the rack-identifying machine readable label when the rack is placed into said rack-receiving location disposed adjacent to said label reading device to obtain receptacle data for each receptacle having a machine-readable label and to obtain rack identifying data;
      store the receptacle data and the rack identifying data and associate the receptacle data with the rack identifying data;
      read the rack-identifying machine readable label when the rack is placed in one of the other rack-receiving locations to obtain rack identifying data;
      acquire location data identifying the other rack-receiving location in which the rack was placed; and
      retrieve the stored receptacle data that is associated with the rack-identifying data and associating the retrieved receptacle data with the location data to thereby associate the retrieved receptacle data with the rack-receiving location in which the rack was placed.

2. The apparatus of claim 1, wherein the machine readable labels are barcode labels and the label reading device is a barcode reader.

3. The apparatus of claim 1, wherein each rack-receiving location comprises a linear track adapted to receive a rack configured to hold a plurality of receptacles in an aligned orientation.

4. The apparatus of claim 1, wherein said data processing system is further configured to provide an indication of the rack-receiving location in which a rack should be placed.

5. The apparatus of claim 1, further comprising a rack configured to hold one or more receptacles and including a rack-identifying machine-readable label.

6. The apparatus of claim 3, wherein the linear track is adapted to engage a guide track formed in the rack.

7. The apparatus of claim 1, wherein the apparatus further comprises a bay comprised of a structure that, at least partially, encloses the plurality of rack-receiving locations.

8. The apparatus of claim 7, wherein the temperature of the area enclosed by the structure can be altered to a temperature that is different than a surrounding ambient temperature.

9. The apparatus of claim 1, wherein each at least one receptacle is configured to contain a fluid biological sample.

10. An apparatus for reading machine-readable labels disposed on receptacles and associating receptacle data read from each machine-readable label with a location within the system, said apparatus comprising:
   a plurality of rack-receiving locations, each configured to receive a rack holding at least one receptacle;
   a label reading device configured to read a rack-identifying machine-readable label disposed on the rack and a machine-readable label disposed on the at least one receptacle held on the rack, wherein said label reading device is disposed adjacent to a first of said rack-receiving locations; and
   a data processing system, which includes data storage media and is configured to:
      read the machine-readable label of each receptacle having a machine-readable label and read the rack-identifying machine readable label when the rack is placed into said first rack-receiving location to obtain receptacle data for each receptacle having a machine-readable label and to obtain rack identifying data;
      store the receptacle data and the rack identifying data and associate the receptacle data with the rack identifying data;
      read the rack-identifying machine readable label when the rack is placed in a second of said rack-receiving locations to obtain rack identifying data, wherein the first and second rack-receiving locations are different locations;

acquire location data identifying the second rack-receiving location in which the rack was placed; and retrieve the stored receptacle data that is associated with the rack-identifying data and associating the retrieved receptacle data with the location data to thereby associate the retrieved receptacle data with the rack-receiving location in which the rack was placed.

11. The apparatus of claim 10, wherein the machine readable labels are barcode labels and the label reading device is a barcode reader.

12. The apparatus of claim 10, wherein each rack-receiving location comprises a linear track adapted to receive a rack configured to hold a plurality of receptacles in an aligned orientation.

13. The apparatus of claim 10, wherein said data processing system is further configured to provide an indication of the rack-receiving location in which a rack should be placed.

14. The apparatus of claim 10, further comprising a rack configured to hold one or more receptacles and including a rack-identifying machine-readable label.

15. The apparatus of claim 12, wherein the linear track is adapted to engage a guide track formed in the rack.

16. The apparatus of claim 10, wherein the apparatus further comprises a bay comprised of a structure that, at least partially, encloses the plurality of rack-receiving locations.

17. The apparatus of claim 16, wherein the temperature of the area enclosed by the structure can be altered to a temperature that is different than a surrounding ambient temperature.

18. The apparatus of claim 10, wherein each at least one receptacle is configured to contain a fluid biological sample.

* * * * *